US008515528B2

(12) United States Patent
Graser et al.

(10) Patent No.: US 8,515,528 B2
(45) Date of Patent: Aug. 20, 2013

(54) MEASURING ARRANGEMENT AND METHOD FOR THE THREE-DIMENSIONAL MEASUREMENT OF AN OBJECT

(75) Inventors: Rainer Graser, Ulm (DE); Raimund Hibst, Erbach (DE); Karl Stock, Ellwangen (DE); Michael Zint, Ulm (DE)

(73) Assignee: Degudent GmbH, Hanau (DE)

( * ) Notice: Subject to any disclaimer, the term of this patent is extended or adjusted under 35 U.S.C. 154(b) by 714 days.

(21) Appl. No.: 12/532,262

(22) PCT Filed: Apr. 24, 2008

(86) PCT No.: PCT/EP2008/054982
§ 371 (c)(1),
(2), (4) Date: Sep. 21, 2009

(87) PCT Pub. No.: WO2008/129073
PCT Pub. Date: Oct. 30, 2008

(65) Prior Publication Data
US 2010/0099984 A1    Apr. 22, 2010

(30) Foreign Application Priority Data
Apr. 24, 2007  (DE) .......................... 10 2007 019 267

(51) Int. Cl.
*A61B 6/00*    (2006.01)
(52) U.S. Cl.
USPC ........................................................ 600/476
(58) Field of Classification Search
USPC ................. 600/476; 356/303, 309, 317, 319, 356/322, 324, 340, 616
See application file for complete search history.

(56) References Cited

U.S. PATENT DOCUMENTS

| | | |
|---|---|---|
| 6,028,306 A | 2/2000 | Hayashi |
| 6,867,406 B1 | 3/2005 | Fairley et al. |

FOREIGN PATENT DOCUMENTS

| | | |
|---|---|---|
| DE | 1963594 | 2/1998 |
| DE | 10242374 | 4/2004 |
| DE | 10321885 | 12/2004 |
| DE | 102006007170 | 8/2007 |
| EP | 0321529 | 6/1989 |
| EP | 0466979 | 1/1992 |
| JP | 03-223709 | 10/1991 |
| JP | 08-233544 | 9/1996 |
| JP | 2005-069827 | 3/2005 |
| WO | 2007/090865 | 8/2007 |

*Primary Examiner* — Unsu Jung
*Assistant Examiner* — Saurel J Selkin
(74) *Attorney, Agent, or Firm* — Ladas & Parry, LLP

(57) ABSTRACT

A measuring arrangement and a method for the three-dimensional measurement of at least part of an object includes a light source with a continuous spectrum, a device for generating a multifocal lighting pattern, a lens with a large chromatic aberration for imaging foci of the lighting pattern on the object, a detection unit for generating the wavelength spectrum of the foci that are confocally imaged on the object via the lens, and a spectrum-dispersive device disposed between the confocally imaged foci and the detection device. In order to create a highly accurate surface profile in a relatively short time even in the case of moving objects, the invention proposes that a first hole pattern including first holes be disposed in the plane of the confocally imaged foci, the geometric arrangement of the first holes corresponding to the geometric arrangement of the foci of the multifocal lighting pattern.

42 Claims, 4 Drawing Sheets

MEASURING ARRANGEMENT AND METHOD FOR THE THREE-DIMENSIONAL MEASUREMENT OF AN OBJECT

The invention relates to a measuring arrangement for three-dimensional measuring of at least one part on an object, in particular a semitransparent object, comprising one light source with a continuous spectrum, one device to generate a multi-focal illumination pattern, an objective lens with high chromatic aberration to image foci of the illumination pattern onto the object, a detector unit such as a CCD chip to determine the wave length spectra of the foci imaged confocally onto the object via the objective lens, as well as one spectrum dispersing device that is arranged between the confocally imaged foci and the detector unit.

The invention further relates to a method for measuring the shape of at least one section of an object, in particular a semitransparent object such as at least a section of a tooth, utilizing one light source to generate light with a continuous spectrum, one device to generate a multi-focal illumination pattern, one objective lens with high chromatic aberration to image foci of the illumination pattern onto the object, one detector unit to determine the wave length spectra of the foci imaged confocally onto the object via the objective lens, whereby from the respective wavelength spectrum the spectral peak position of each focus is determined, from which subsequently one computes the extent of the object along the direction of the imaging ray (Z coordinate).

In many technical fields it is necessary to determine, i.e. measure, the three-dimensional structure of objects. One example is the determination of the shape of a tooth, which is necessary to produce a dental prosthesis. For dental reconstructions that are still produced by conventional methods using a plaster cast, one endeavours to leave behind the corresponding classical method and to determine the geometry of the dental shape using a non-contacting method.

A large number of methods for the acquisition of the three-dimensional structure of bodies are known in the art. Of the existing optical methods one has to mention the strip projection method or phase shift method, optical coherence tomography, and holography. In the field of dentistry, the phase-shift method already finds practical application.

However it has come to light that corresponding optical methods do not produce the desired results, in particular for objects with high scattering characteristics. In the strip projection method, for example, scatter leads to a lack of definition of the strips and consequently to lower resolution.

Also known are methods in which the object is not illuminated in its entirety, but rather only in one region with one sharp focus or several foci utilizing confocal imaging. To obtain a complete two-dimensional image, the focus or foci must be scanned across the object. To measure three-dimensional structures, it is necessary to shift the focal plane along the axial direction.

Alternatively, a wide-band light source and a suitable optical system with a highly wave-length-dependent focal length can be employed to image the focus or the foci. As a result, the foci are sharply imaged at different distances from the objective lens in dependence on their wavelength. After imaging the foci backwards through the objective lens, an intensity maximum can be detected in the focus plane for the particular colour that is sharply imaged at the corresponding object distance. Thus, determining the spectral peak position allows one to determine the distance between the object and the objective lens at this point, and consequently and ultimately allows determining the three-dimensional structure of the object. Evaluation is performed either by points using a spectrometer or by lines using a line spectrometer with camera chip.

EP-B-0 321 529 discloses a measuring arrangement for measuring the distance from an objective lens with high chromatic aberration to an object. For detection one employs a black & white CCD chip camera, in front of which is arranged a spectrum-dispersing device that possesses an input slit. This converts the wavelength information for every point to position information to obtain a profile image of the surface of the object.

EP-B-0 466 979 relates to an arrangement for simultaneous confocal image generation. For this purpose one uses a matrix of punched holes such as a Nipkow disk to generate points of light, which are imaged in focus onto an object. A CCD array camera is used as detector unit.

Described in DE-A-102 42 374 is a confocal distance sensor with an imaging optical system with chromatic aberration, which is intended for inspection purposes in the electronics field. As a light source one can employ a light source with a multitude of point light sources. As a light detector one employs point detectors, whereby one point detector is assigned to each point light source and they are arranged confocal relative to each other.

Known from DE-A-103 21 885 is a confocal measuring arrangement for the three-dimensional measuring of an object using chromatic fine splitting, in which a multitude of foci is generated by means of a micro-lens array and is imaged onto the object. The reflected light is focussed back onto the plane of the micro-lens foci. This arrangement is used to measure two- or three-dimensional micro-profiles of objects to be measured or two- or three-dimensional transparency or reflectivity profiles.

The present invention is based on the objective to further develop a measuring arrangement as well as a method for the three-dimensional determination of the shape of an object, particularly a semitransparent object such as a tooth, in such a way, that a highly precise surface profile can be established in a short timeframe even for moving objects. It is in particular desirable to be able to measure scattering or highly scattering objects that exhibit a very high white-light background, which would facilitate application in the field of dentistry.

As a solution to this problem, in a measuring arrangement of the above-mentioned type it is chiefly intended that in the plane of the confocally imaged foci be arranged one first matrix of holes with first holes, whereby the geometric arrangement of the first holes corresponds to the geometric arrangement of the foci of the multi-focal illumination pattern.

Different from arrangements known in the art, a matrix of holes or a pinhole array is arranged in the focal plane—where the foci reaching the object are imaged—of the objective lens with high chromatic aberration, whereby consequently the illumination pattern is confocally imaged back from the measured object onto this matrix of holes or pinhole array. In this, the geometric correspondence of the first holes of the first matrix of holes relative to the illumination pattern is tuned so that a unique assignment is made, so that as a result the foci in the holes of the matrix of holes can be assigned positional coordinates in a plane that extends normal to the beam path passing through the objective lens.

According to the invention, holes or pinholes distributed across an area are positioned in the focal plane of the objective lens and the illumination pattern is confocally imaged back from the object into these holes or pinholes. In this, the foci that are imaged on the object are imaged—in dependence on wavelength and the distance between the objective lens and the object—onto the pinhole. The spectra of these foci are subsequently read out by the detector device. In this, the invention in particular intends that the dispersing device arranged upstream of the detector device laterally spreads the spectral lines of the focus imaged in the respective hole, before the spectral lines reach pixels of the detector device. For this purpose it is intended that the detector device comprises the pixels of a CCD chip sensor that are arranged in an area, whereby the dispersing device extends at such an inclination relative to the first matrix of holes and the detector device that the laterally spread spectra can be imaged onto the pixel area without any overlap. In this, it is in particular intended that the spread spectra impact the pixel area in such a manner that consecutive laterally spread spectra contact each other without any free pixels.

The following should be noted with regard to the inclination of the spectrum-dispersing device: the direction of the spectral spread by the spectrum-dispersing device forms an angle of for example 6.5° relative to a line connecting neighbouring points, so that the pixel path that is available for spectral expansion and interpretation is greater than the distance between neighbouring pinholes. The tilt of the optical axis after the spectrum-dispersing device such as a dispersion prism is 15°, for example.

The invention consequently proposes a colorimetry unit that consists of one dispersing element for the spectral dispersion of the light of every pinhole along a line and one CCD chip, on which the spectrally dispersed measuring points are imaged. This results in an arrangement similar to a line spectrometer, with the difference being that the measurement points are not arranged on a line but rather are arranged uniformly across the entire measuring area. The individual holes of the pinhole array correspond to a long slit of a line spectrometer.

In this, the illumination pattern is coordinated with the colorimetry unit in such a manner, i.e. it is chosen so that the clear spaces between the individual foci are used for the spectral decomposition of the light and for measurements along lines.

Corresponding to the illumination pattern, one obtains with each image record several nodes, i.e. measurement points, distributed across the measuring section. If the distance between nodes is larger than the desired resolution, it will be necessary to shift the illumination pattern accordingly. This can be performed either using a suitable optical element such as a plane-parallel plate in the measuring arrangement or by way of a continuous motion of the measuring arrangement itself, whereby the resulting individual images are combined to form a complete image.

While the arrangement of holes in the matrix of holes or pinhole array specifies the spatial coordinates in a plane running normal to the beam path passing through the object lens, spectral evaluation of the focus that is imaged in the respective hole will determine the required height information as Z coordinate, since the foci—in dependence on the wavelength—are sharply imaged at different distances from the objective lens and only those foci are imaged in the holes of the pinhole array that themselves were imaged on the object.

In order to generate an illumination pattern, it is for example intended that arranged downstream of the light source be a micro-lens array for generating the multi-focal illumination pattern in the first focal plane on the light-source-facing side of the objective lens. But it is also possible to position in the first focal plane of the objective lens a second matrix of holes, in whose holes the foci of the multi-focal illumination pattern can be imaged or whose holes themselves define the multi-focal illumination pattern.

To image the foci in the plane of the first matrix of holes, a first beam splitter is arranged between the objective lens and the detector device. A second beam splitter can additionally be positioned between the objective lens and the illumination pattern, in particular between the objective lens and the first beam splitter, in order to obtain a live image of the object. Hereby it is preferably intended that the object be illuminated using a second light source, whereby the spectral range of the second light source also can be outside of the wavelength region of the first light source, which chiefly is evaluated to acquire the shape of the object. The live image can be recorded via a camera.

Independent thereof, the optical design of the second beam splitter should be such that it exhibits high transmission for the light for the confocal imaging of the foci. If for generating the live image one uses a spectral region that is outside of the wavelength range of the first light source, then the second beam splitter preferably will be a dichroic filter, which in addition to a high transmission efficiency for the light of the first lighting source, possesses a high reflectance for the light of the second light source. For obtaining a live image that is as sharp as possible, it is of advantage if the spectral region used for the recording is as narrow as possible, which can be accomplished either by using a spectral filter inserted in front of the camera or camera chip and/or through the use of a narrow-band second light source.

However, it should be noted that it is not absolutely necessary to employ a second light source. Rather, the foci imaged onto the object can be sufficient to generate a live image.

As a further development of the invention it is intended that the first matrix of holes possess second holes, which are associated with the first holes, are intended for the purpose of determining the background of the measurement results, and are positioned outside of the illumination pattern.

To achieve a compact unit, it is intended that a beam-deflecting device such as a mirror be provided between the objective lens and the object, resulting in a structurally simple system for the intraoral use of the measuring arrangement.

In particular, the first light source is a halogen lamp. But it is also possible to use white-light LEDs or several coloured LEDs.

An alternative option is to feed the emission of the first light source through fibre-optic light guides, whose output ends are located in the first object plane of the objective lens and consequently themselves represent the foci, in place of the foci of the micro-lens array. Alternatively, the output end of preferably one fibre-optic light guide is located in the focus plane of one collimating optical system, behind which the now collimated beam of the fibre-optic light guide reaches the micro-lens array.

In order to obtain an unambiguous geometric correspondence between the image pattern and the first matrix of holes and the first beam splitter arranged in between it is intended that the micro-lens array, the first matrix of holes, and the first beam splitter be embodied as a single constructional unit. In particular, this yields a cube-shaped geometry.

To be able to measure different sections of the object in an uncomplicated manner, one can position between the first beam splitter and the objective lens one or several plane-parallel plates that are rotatable or tiltable accordingly. In particular, if a plane-parallel plate is present, it will be arranged rotatable around two axes running in the plane defined by the plate.

It is also possible to arrange the deflecting mirror in a movable and/or rotatable manner to be able to measure different sections of the object.

A method of the above-mentioned type is characterized in that arranged in the plane of the confocally imaged foci is a first matrix of holes with first holes, whose geometric arrangement correlates with that of the multi-focal illumination pattern, and in that the position of the first holes defines positions of the foci on the object in a plane (X,Y coordinates) extending normal relative to the imaging beam, whereby the wavelength spectra of the foci imaged in the holes are acquired simultaneously by the detector device.

In this it is intended that the wavelength spectrum of every focus imaged in a hole be laterally spread out by a dispersing device arranged downstream of the first matrix of holes.

In particular, the invention proposes that the detector device comprise a pixel area of a CCD sensor for acquiring the wavelength spectra and that the pixel area and/or the dispersing device be inclined relative to the first matrix of holes in such manner that the wavelength spectra of the foci imaged in the first holes impact the pixel area without any overlap.

In this, the pixel area and the dispersing device should be aligned relative to the first matrix of holes in such a way that the wavelength spectra of the foci imaged in the first holes contact each other without any overlap.

To be able to determine the wavelength of the foci imaged sharply in the individual holes to an adequate extent and with the necessary accuracy, it is intended that a first spectrum be obtained from a focus, that an optical element changing the path length of the optical path be inserted into the beam path of the focus, that a second spectrum be obtained of the focus with changed optical path, that the spectra be subtracted from each other, and that the wavelength of the light of the focus be determined from the resulting equal peaks with opposite signs.

In accordance with a further suggestion for the determination of the peak of the measuring curve that characterizes the wavelength or wavelength range of the focus, it is intended for the purpose of background determination that the spectral curve of the background of the spectrum of the focus be determined by measuring spectra of light reaching second holes associated with the first holes, whereby the positions of the second holes deviate from those of the multi-focal illumination pattern. In this, one preferably averages the spectra of several second holes associated with one first hole to determine the background.

If successive sections of the object are being measured in order to measure the entire object, then consecutive sections should comprise a common subsection, which should amount to 50% to 95% of the respective section. This allows a simple correlation between the individual measurements. It is further intended that for the purpose of determining the shape of at least one portion of the object, the sections be consecutively recorded with a frame rate of between 25 and 50 pictures per second.

Preferably the measuring method is intended for the intraoral measuring of teeth or sections of teeth. For this purpose, the objective lens together with the deflecting device can be inserted into the mouth to carry out the measurements.

Further details, advantages, and features of the invention are not only found in the claims, the characteristic features contained therein—on their own and/or in combination—, but also in the description of the preferred embodiment examples illustrated in the figures.

The figures, in which identical elements always carry the same reference labels, illustrate different variants of measuring arrangements, to be used in particular to intraorally scan one tooth or zones thereof or several teeth or zones thereof, in order to acquire the three-dimensional shape. In this, the shape-representing data is made available in digital form, so that subsequently a dental prosthesis can be manufactured in the usual manner from in particular presintered ceramic blanks using CAD/CAM technology.

Figure 2:
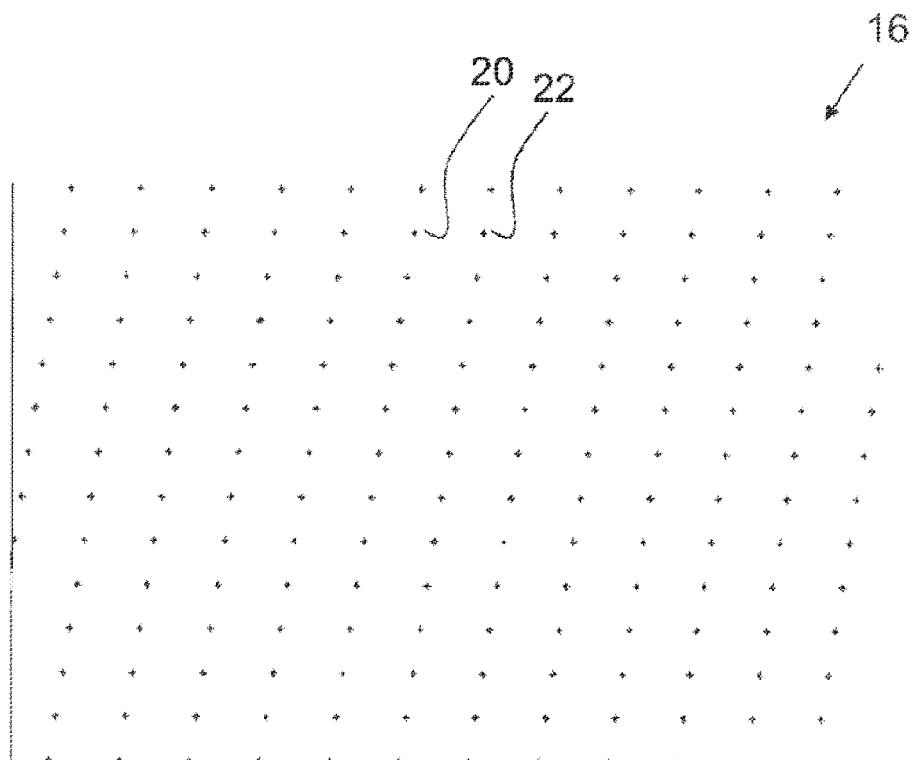
FIG. 2 shows an illumination pattern.

The measuring arrangement comprises among the essential elements one light source 10 such as a halogen lamp, whose light is collimated by a lens 12. The collimated light beam reaches a micro-lens array 14, which images an illumination pattern 16 into the focal plane of an objective lens 18 with high chromatic aberration. The illumination pattern generated by the micro-lens array 14 can for example possess a size of 20 mm×15 mm with approximately 1600 foci or for example a size of 5 mm×6.5 mm with approximately 2000 foci at a spacing of 250 μm. FIG. 2 illustrates purely as an example the corresponding illumination pattern 14, in which as an example two foci carry the reference labels 20, 22.

The illumination pattern 16 can be designed in such a manner that the resulting diameter of each of the foci 20, 22 will be approximately 25 μm or approximately 12 μm.

To improve the illumination pattern, the micro-lens array 14 can be combined with a matched pinhole array, which is positioned in the object plane of the objective lens 18. In this, the holes of the pinhole array correspond with respect to geometry or position to the illumination pattern formed by the foci 20, 22.

Figure 1:
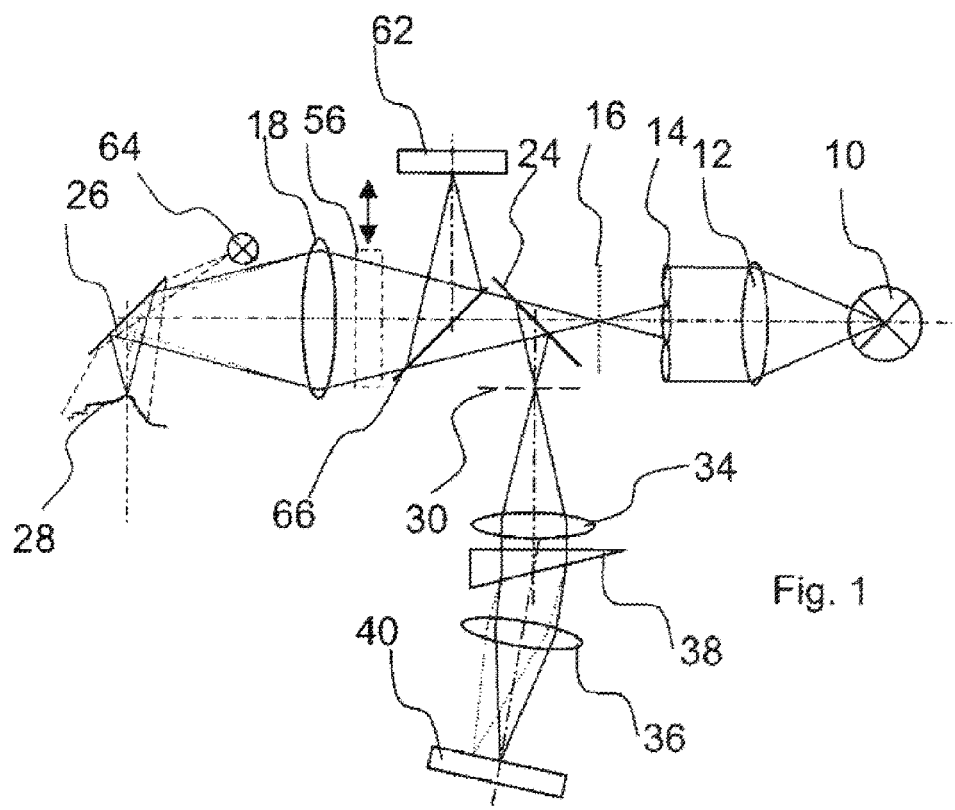
FIG. 1 shows a schematic illustration of a first variant of a measuring arrangement.

In accordance with the illustration of FIG. 1, the light originating from the light source 10 downstream of the illumination pattern 16 reaches a beam splitter 24, from which the transmitted fraction reaches the objective lens 18 with high chromatic aberration.

In the illustration of the figure, the beam splitter 24 is shown as a plate with a partially reflecting layer. But other beam-splitting elements are alternatively possible. Beamsplitter cubes should be mentioned as an example. Also envisioned can be ring-shaped mirrors or smaller mirrors, whereby the outer or inner beam components, respectively, can serve for the detection or illumination to be explained in the following.

The beam passing through the objective lens 18 is imaged via a deflection device 26 such as a deflecting mirror onto an object 28 to be measured, such as a tooth. In this, the distance between the plane of the illumination pattern 16 and the object 28 is chosen so that the foci—after deflection by the deflecting device 26—are imaged onto the surface of the object 28, whereby depending on the distance of the object's surface from the objective lens 18, different colours, i.e. wavelengths, are imaged sharply in focus. In this, the size of the measuring area and the resolution are determined by the chosen image scale.

Part of the radiation, i.e. light, emitted by the object 28, falls back into the objective lens 18 and after partial reflection at the beam splitter 24 falls onto a first matrix of holes or pinhole array 30, whose holes correspond—with respect to the separation of holes and the size and overall geometric arrangement—to the arrangement of the illumination pattern 16.

In other words, the axial and lateral position of the pinhole array 30, i.e. its holes, is chosen so that the foci on the surface of the object 28 are imaged confocally in the holes of the pinhole array 30. Consequently, each hole of the pinhole array 30 defines the X and Y coordinates of the respective focus imaged on the surface of the object 28.

Figure 5:
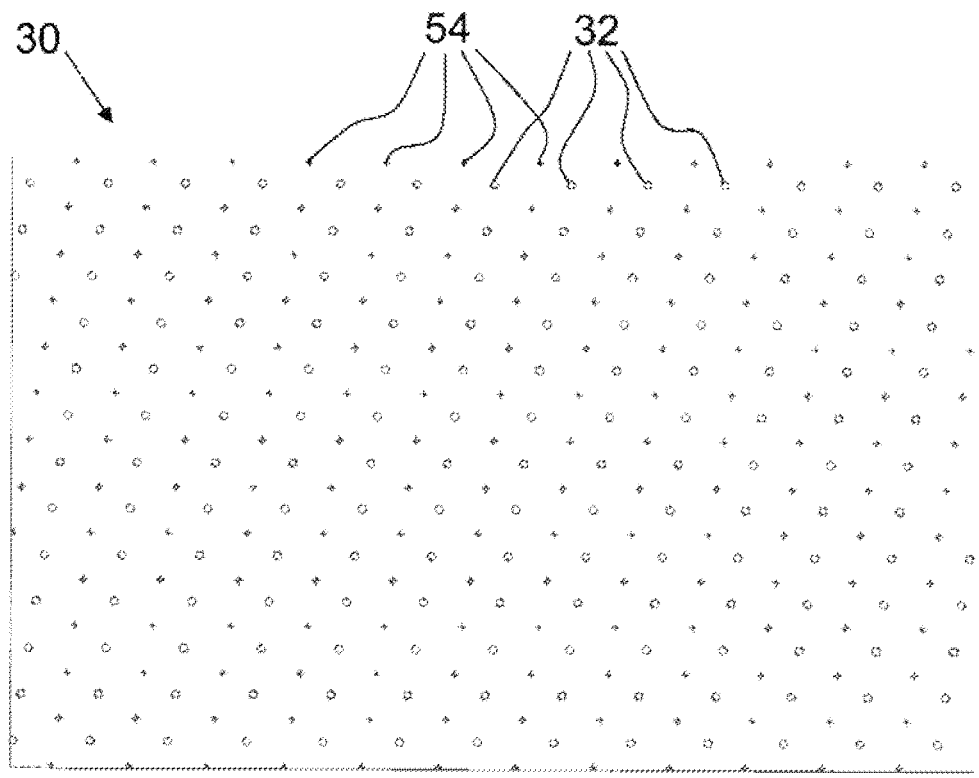
FIG. 5 shows a matrix of holes with first holes and second holes.

FIG. 5 illustrates a configuration of the pinhole array 30, whereby both the positioning and extent of the open circles 32 correspond to the pattern of the foci of the illumination pattern 16.

Because of the high chromatic aberration of the objective lens 18, in each case only one colour will be imaged sharply at the respective measuring point defined by the position of the foci of the illumination pattern 16—depending on its distance from the object 18—i.e. only one wavelength satisfies the confocality condition. Correspondingly, an intensity maximum is observed at this wavelength in the spectrum of the light transmitted through the respective hole 32 of the pinhole array 30.

As the measuring points become more densely spaced and as the light emission of the object 28 increases, an increasing proportion of white light passes through the hole or pinhole in addition to the peak wavelength. In order to determine the peak wavelength characteristic of this focus to an adequate degree and with the required accuracy despite this obstacle, it is intended that behind the pinhole array 30 be arranged a spectrometric arrangement corresponding to the illumination pattern 16 and thus the matrix of holes of the pinhole array 30, which in the embodiment example consists of the optical systems 34, 36 and a spectrum-dispersing element, e.g. a prism 38, arranged between them.

The pinhole array 30 is imaged onto a CCD chip sensor, which is used as detector device 40, by the optical systems 34, 36, which can consist of one or several lenses. The spectrum-dispersing element, i.e. the prism 38, effects a lateral spectral spreading of the maximum-intensity wavelength region of the light of the focus that appears in the holes with maximum intensity, so that consequently every hole of the pinhole array 30 is imaged onto a line on the CCD chip sensor 40, i.e. the pixels arranged in an array, whereby—as in a line spectrometer—the position along this line corresponds to a particular wavelength. In this, the spectrum-dispersing unit—consisting of the optical systems 34, 36 and the prism 30—and the CCD sensor 40 are positioned relative to the pinhole array 30 in a manner so that the laterally spread spectral lines from consecutive holes of the pinhole array 30, which now form lines on the pixels, contact each other without or nearly without empty spaces and without any overlap taking place.

Figure 3:
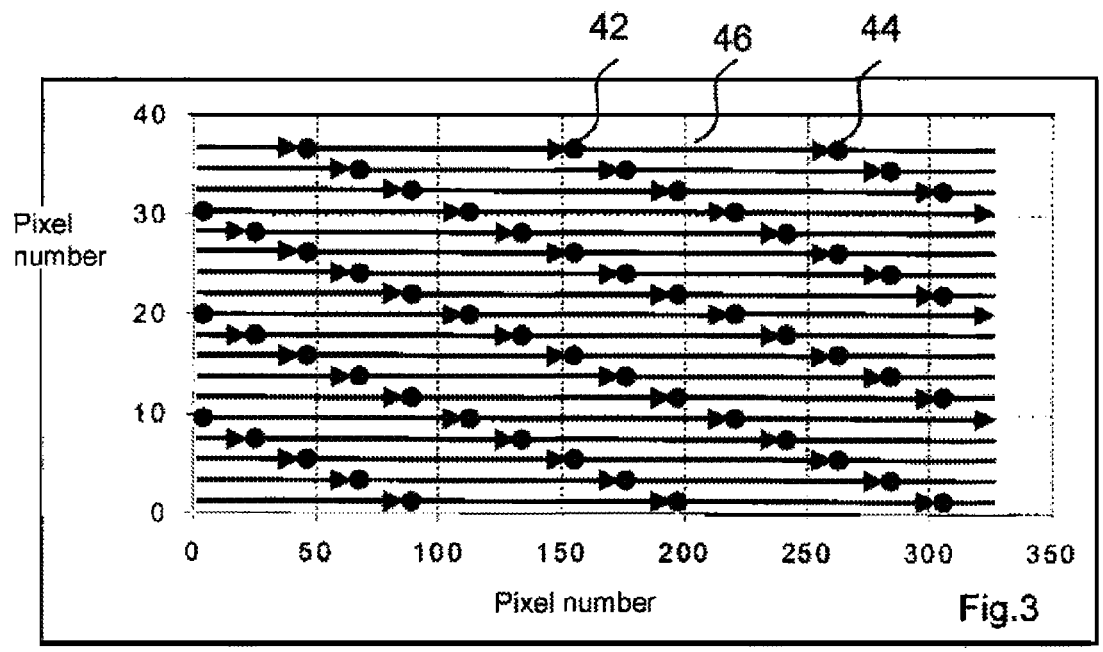
FIG. 3 shows a spectral distribution.

FIG. 3 illustrates that all pixels between the measurement points are used for the spectral dispersion and thus for the determination of the peak position. The filled circles 42 represent a measurement point and the arrow 46 extending towards the following measurement point 44 represents the laterally dispersed spectral lines of the focus imaged in the hole of the pinhole array that corresponds to the measurement point 42.

If for example one chooses the above-specified illumination pattern with the stated dimensions and a CCD chip or camera chip with a size of 6.4 mm×4.8 mm and with 1 million pixels (pixel size 6.7 µm×6.7 µm), then 186 pixels are available for the spectral dispersion per measuring point. Given a line width of 2 pixels which corresponds to the pinhole diameter, one obtains for each of the approximately 2000 measuring points and approximately 2000 background points a line spectrometer with 93 elements for spectral dispersion. After image acquisition, the evaluation of the image information or measurement data takes place either on the CCD sensor itself or on an external unit. For this, a suitable algorithm is used to determine for every measuring point the spectral peak position and from this the distance of each measuring point to the object 28. In this manner, one image yields the three-dimensional structure of the object 28 at the nodes or measuring points, whereby the resolution depends on the chosen focus distance and the image scale of the objective lens 18.

If the separation of nodes is greater than the desired resolution and/or if the three-dimensional structure can not be acquired from a viewpoint, the illumination pattern 16 can be shifted accordingly. If the measuring arrangement is a manually operated device, then a complete acquisition of the object 28 can be achieved through a continuous moving of the measuring arrangement, whereby the resulting individual images are fit together to form a complete image in a suitable manner.

Since, as mentioned before, in the case of an object 28 causing scatter, not only the wavelength of the sharply imaged focus is imaged in the holes 32 of the pinhole array 30, but also a significant amount of white light, it becomes necessary to employ methods to eliminate or reduce the background caused by this.

Figure 4:
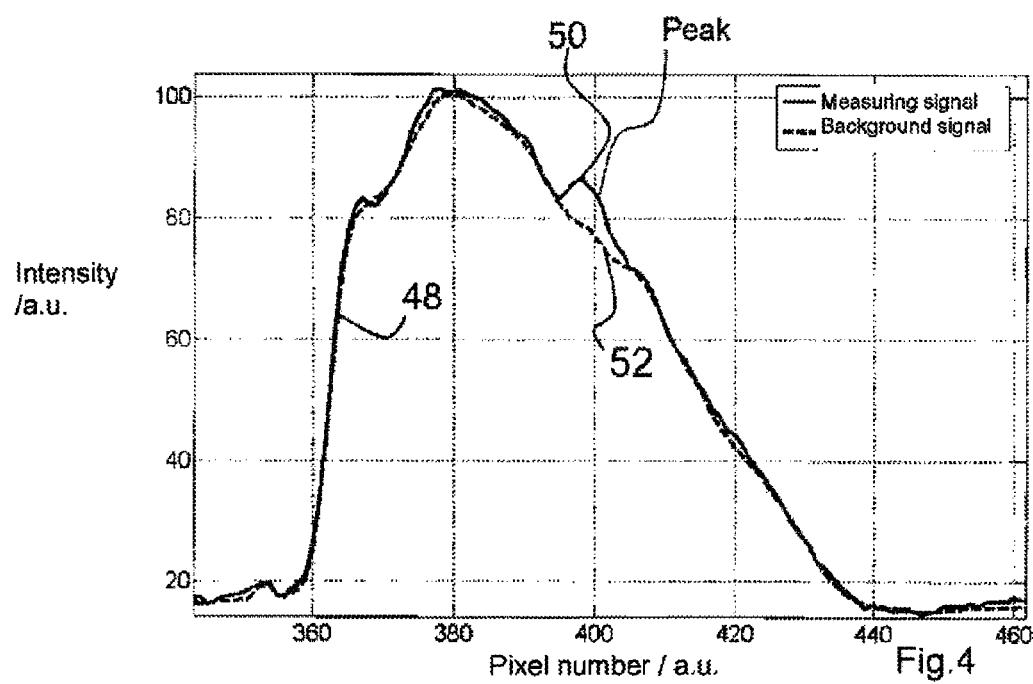
FIG. 4 shows a measurement curve.

For the purpose of illustrating the importance of the white-light background during measuring and evaluation, FIG. 4 shows a typical measuring signal 48 with the object 28 being a tooth. The higher the portion of white-light background in the measuring signal 48 is, the more accurate must be the information on the spectral behaviour of the background 52 in each measured point to be able to determine the position of the peak 50 that is characteristic of the wavelength of the focus. For this purpose a method can be employed that is schematically illustrated in FIG. 5. In addition to the holes 32, in which the foci are imaged, the pinhole array 30 comprises additional holes 54 that are not matched to the illumination pattern 14. In accordance with the preferred arrangement of FIG. 5, the holes 54 that do not correspond to the illumination pattern 14 are positioned between the holes 32 that do correspond to the illumination pattern 14. The spectra in the holes 54, in which no foci are imaged, thus approximately represent the background signal of the neighbouring holes 32, in which foci are imaged and which represent measuring points. In this, one alternatively can use the measuring signal of an individual neighbouring hole 54, which basically contains only white light, or the average of several neighbouring holes 54, to determine the background 52. The holes 54 can be referred to as non-illuminated whereas the holes 32 can be referred to as illuminated holes or pinholes.

In accordance with the arrangement of the illuminated or first holes 32, in which foci are imaged, and the second holes 54 used for determining the background, which can also be referred to as non-illuminated holes, only half the number of pixels is available per measuring point for spectral dispersion, compared to the variant, in which the number of foci is identical to the number of pinholes or holes 32.

Figure 8:
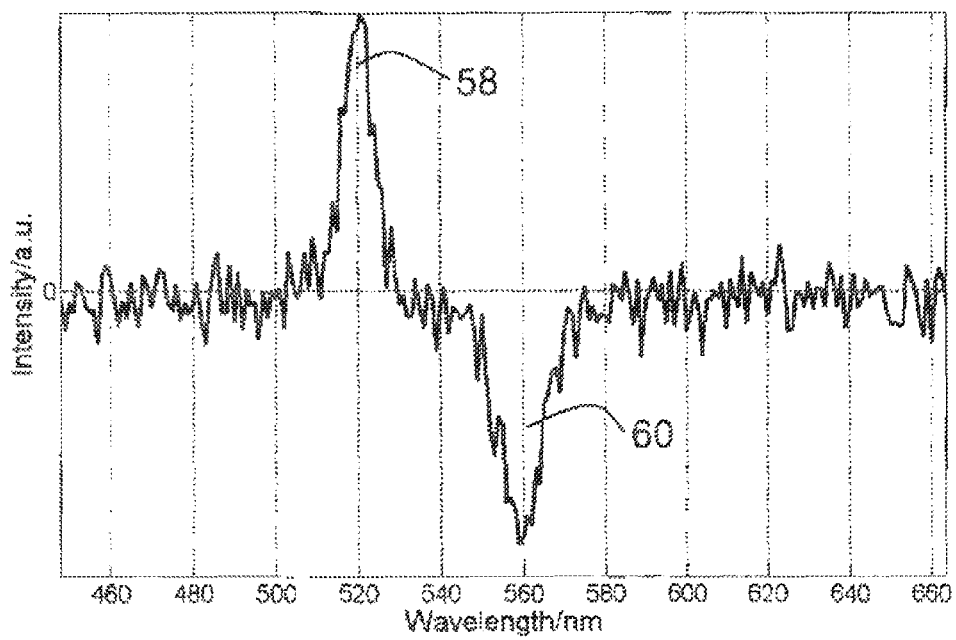
FIG. 8 shows peak positions obtained by subtraction of two measurement curves.

It is further possible to determine the white-light content by using a plane-parallel plate 56, which is arranged in the beam path between the first beam splitter 24 and the beam deflector 26, in particular between the objective lens 18 and the first beam splitter 24. The plane-parallel plate 56 in the optical path effects an axial shifting of the foci, which in turn effects a shift of the peak position in the measured signal. By sequentially acquiring images at one position with and without the plane-parallel plate 56 one obtains per measuring point two spectra with different peak positions but identical background. Subtracting the two spectra thus allows eliminating the background. A typical signal curve after subtraction of the two spectra is illustrated in FIG. 8. One recognizes the peaks 58, 60, which were determined by the subtraction and whose separation is predetermined by the plane-parallel plate 56.

In the further evaluation for determining the unknown object distance, one can employ several characteristic quantities, among others the two extrema, i.e. peaks 58, 60 and/or the spectral position of the zero passage.

Live-image acquisition can be provided as a positioning aid and as an aid for assigning the individual images to a complete picture. For this purpose the embodiment example possesses an additional camera chip 62, onto which the object 28 is imaged. An additional light source 64 can be provided, which preferably illuminates the object 28 via a deflection device 26. Instead of one light source 64 it is possible to have several light sources. For live-image acquisition the light source 64 should emit light in a spectral region that is outside of the wavelength range used for the actual measurements. This allows carrying out live imaging and measuring independently from each other.

For the purpose of beam splitting one can employ in the beam path between the objective lens 18 and the first beam splitter 24 a second beam splitter 66 such as a dichroic filter, which provides high transmission for the measuring signal and high reflection for the live-image signal.

As mentioned above, the objective lens 18 is also used to image the object 28 onto the camera chip 62, whereby the axial position of the camera chip 62 is chosen so that the live image is in focus approximately in the centre of the measuring region.

The size and shape of the measuring arrangement or the measuring device is particularly important in the case of intraoral application for measurement of teeth. Thus, in a development of the invention, it is possible that only the objective lens 18 and the beam-deflector 26 are arranged in an intraoral part of a hand-held device, which can be inserted into the mouth. The other components can be integrated in an extraoral part of the hand-held device or in a separate equipment unit. A compact light source offers the option of integration in a hand-held device.

Instead of the halogen lamp 10, one can also envision other light sources, such as for example one white-light LED or several LEDs of different colours with a suitable collimating optical system. Alternatively the light source 10 can be integrated in an external unit and the light is fed into the hand-held unit via fibres, whereby the output end of the fibre-optic light guide is positioned at the focal point of the collimator lens 12, or the output ends of several corresponding fibre-optic light guides themselves represent the foci of the illumination pattern, instead of the foci of the micro-lens array.

For generating the multi-focal illumination pattern 16 it is also possible to use—instead of or in addition to the micro-lens array 14—a pinhole array that can be arranged in the plane of the illumination pattern 16 shown in the figures.

Figure 6:
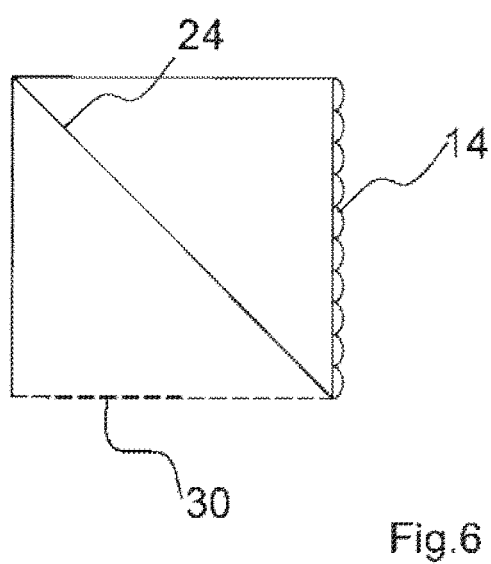
FIG. 6 shows a monolithic variant of a micro-lens array and pinhole array with beam splitter.

It is essential for an exact measuring process and uncomplicated handling of the measuring device that there exists a precise geometric and spatial correspondence between the micro-lens array 14 and the pinhole array 30. To translate this into practice, one can choose a monolithic design, which is schematically illustrated in FIG. 6. Also integrated into the monolithic embodiment, which can possess a cube-shaped geometry, is the first beam splitter 24.

If the object 28 is not measured or scanned by a single picture but rather by a multitude of pictures, i.e. using individual images, the images must have an unambiguous relation with respect to each other to facilitate an uncomplicated interpretation. For this purpose it is particularly intended that the individual pictures overlap in segments, which constitute 50% to 95% of each picture. As an alternative or supplement it is also possible to use as an aid for the superposition of the individual images the placing of fixed points on the object 28.

As an alternative to the manual displacement of the measuring device, which is preferably embodied—as mentioned above—as a handheld device, actuators can be integrated into the measuring arrangement for the purpose of shifting the measuring points. In this, the highest possibly necessary displacement corresponds to the distance between measuring points minus the desired resolution, consequently 225 µm in the embodiment example being explained (250 µm hole separation-25 µm resolution).

Figure 7:
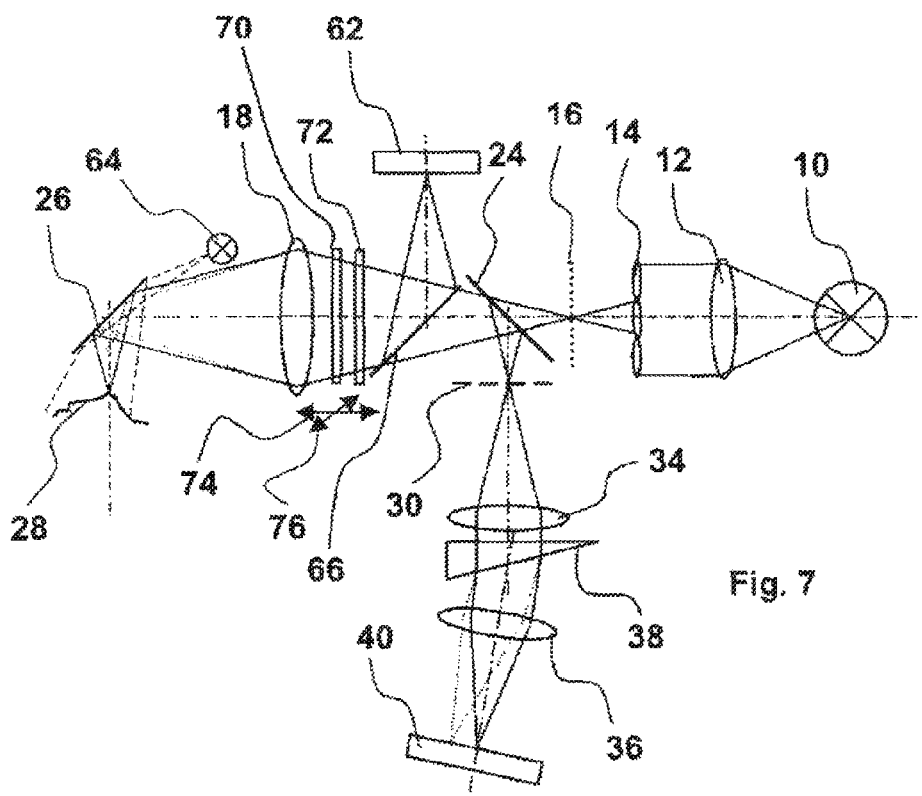
FIG. 7 shows a second variant of a measuring arrangement.

FIG. 7 illustrates an alternative approach for obtaining individual images. Plane-parallel plates 70, 72 can be arranged in the measuring beam—in the embodiment example upstream of the objective lens 18—, whereby it is also possible to use a single plate with two rotational axes (see arrows 74, 76). In this, the axes of rotation preferably run in the plane defined by the plane-parallel plate 70, 72. A further possible variant is the use of a movable or rotatable deflection mirror such as the deflection device 26 as a variable beam-deflection system.

With respect to the live image it should be mentioned that alternatively the use of an additional light source is not necessary, in particular if the illumination pattern is out of focus in the spectral region used for the live-image acquisition.

Furthermore, it is also possible to employ a diffractive element to generate the high chromatic aberration, and/or a diffractive element or a grating as dispersing element, and/or CMOS detectors instead of CCD chips, and/or LCD modulators or DMDs to generate the illumination pattern instead of the micro-lens array.

The invention claimed is:

1. A measuring arrangement for the three-dimensional measuring of at least part of an object (28), in particular a semi-transparent object, comprising one light source (10) with a continuous spectrum, one device (14) for generating a multi-focal illumination pattern (16), one objective lens (18) with high chromatic aberration to image foci of the illumination pattern onto the object, one detector unit (40) for determining the wavelength spectra of the foci imaged confocally onto the object by the objective lens, as well as one spectrum-dispersing device (34, 36, 38) that is arranged between the confocally imaged foci and the detector device, wherein in the plane of the confocally imaged foci is arranged one first matrix of holes (30) with first holes (32), whereby the geometric arrangement of the first holes corresponds to the geometric arrangement of the foci of the multi-focal illumination pattern.

2. The measuring arrangement of claim 1, wherein the dispersing device (34, 36, 38) comprises an optical system that images the foci imaged in the first holes (32) onto the detector device (40), with a dispersing element that laterally spreads the respective spectrum of every focus.

3. The measuring arrangement of claim 2, wherein the imaging optical system comprises two optical systems (34, 36), with the dispersing element (38) positioned in between them.

4. The measuring arrangement of claim 1, wherein the detector device (40) comprises pixels, which are part of a CCD chip sensor and are arranged on an area, and that the spectrum-dispersing device (34, 36, 38) is arranged relative to the first matrix of holes (30) and/or the detector device is arranged relative to the dispersing device in such a manner that the laterally spread spectra impact the pixel surface without overlap.

5. The measuring arrangement of claim 4, wherein the spread spectra impact on the pixel surface in such a manner that consecutive laterally spread spectra contact each other without any free pixels.

6. The measuring arrangement of claim 1, wherein arranged after the light source (10) in the first focus plane extending on the light-source-side of the objective lens (18) is a micro-lens array (14) for generating the multi-focal illumination pattern (16).

7. The measuring arrangement of claim 6, wherein the emission of the first light source (10) is fed through fibre-optic light guides, whose output ends are located in the first object plane of the objective lens (18) and thus the output ends form the foci of the illumination pattern instead of the foci of the micro-lens array.

8. The measuring arrangement of claim 6, wherein the emission of the first light source (10) is fed through one or several fibre-optic light guides, whose output ends are located in the focus plane of a collimating optical system (12), behind which the collimated beam of the fibre-optic light guide reaches the micro-lens array (14).

9. The measuring arrangement of claim 1, wherein arranged in the first focal plane of the objective lens (18) is arranged a second matrix of holes, in whose holes the foci of the multi-focal illumination pattern can be imaged or whose holes define the multi-focal illumination pattern.

10. The measuring arrangement of claim 1, wherein between the objective lens (28) and the detector device (40) is arranged a first beam splitter (24) that deflects light onto the first matrix of holes (30).

11. The measuring arrangement of claim 10, wherein between the first beam splitter (24) and the objective lens (18) is arranged one second beam splitter (66), through which light of the second light source (64) imaging the object (28) can be imaged onto an acquisition device (62).

12. The measuring arrangement of claim 11, wherein the acquisition device (62) is a camera.

13. The measuring arrangement of claim 11, wherein the second beam splitter (66) is of an optical design that ensures high transmission for the light for the confocal imaging of the foci and high reflection for the light of the second light source (64).

14. The measuring arrangement of claim 11, wherein the second beam splitter (66) is a dichroic filter.

15. The measuring arrangement of claim 10, wherein the micro-lens array (14), the first matrix of holes (30), and the first beam splitter (24) are embodied as a single constructional element.

16. The measuring arrangement of claim 10, wherein between the first beam splitter (24) and the objective lens (18) is arranged at least one plane-parallel plate (70, 72), and that the plane-parallel plate is embodied rotatable about two axes running in the plane defined by the plate.

17. The measuring arrangement of claim 1, wherein the measuring arrangement comprises one second light source (64) illuminating the object (28).

18. The measuring arrangement of claim 1, wherein the spectral range of the second light source (64) is outside of the wavelength range of the first light source (10), which can be evaluated to acquire the shape of the object (28).

19. The measuring arrangement of claim 1, wherein the first matrix of holes (30) comprises second holes (54), which are associated with the first holes (32) and are intended for determining the background in the measuring results.

20. The measuring arrangement of claim 1, wherein between the objective lens (18) and the object (28) is arranged a beam-deflecting device (26).

21. The measuring arrangement of claim 20, wherein the objective lens (18) with the beam-deflecting device (26) is a section of the measuring arrangement to be used intraorally.

22. The measuring arrangement of claim 20, wherein the deflection device (26), such as a deflection mirror, is embodied to be moveable and/or tiltable.

23. The measuring arrangement of claim 1, wherein the first light source (10) is a halogen lamp.

24. The measuring arrangement of claim 1, wherein the first light source (10) comprises or consists of white-light LEDs or several coloured LEDs.

25. The measuring arrangement of claim 1, wherein the emission of the first light source (10) is fed through fibre-optic light guides with output ends located in the focus plane of a collimating optical system (12).

26. The measuring arrangement of claim 1, wherein the emission of the first light source (10) is fed through fibre-optic light guides with output ends positioned in the first object plane of the objective lens (18).

27. The measuring arrangement of claim 1, wherein the detector unit possess a cube-shaped geometry.

28. The measuring arrangement of claim 1, wherein the an optical path of the measuring beam can be changed by inserting a plane-parallel plate (56) into the optical path.

29. A method for measuring the shape of at least one section of an object, in particular a semi-transparent object such as at least a section of a tooth, utilizing one light source to generate light with a continuous spectrum, one device for generating a multi-focal illumination pattern, one objective lens with high chromatic aberration for imaging foci of the illumination pattern onto the object, one detector device to determine the wavelength spectra of foci imaged confocally onto the object by the objective lens, whereby the spectral peak position of every focus is determined in each of the respective wavelength spectra, from which is then computed the extent of the object along the direction of the imaging beam, wherein said method comprises:
  arranging, in the plane of the confocally imaged foci, a matrix of holes with first holes, whose geometric arrangement correlates with the arrangement of the multi-focal illumination pattern, and that the positions of the first holes define positions of the foci on the object in a plane extending normal relative to the imaging beam, whereby the wavelength spectra of the foci imaged in the holes are simultaneously acquired by the detector device.

30. The method of claim 29, wherein the wavelength spectrum of every single focus imaged in a hole is laterally spread using a dispersing device arranged downstream of the first matrix of holes.

31. The method of claim 29, wherein the detector device comprises a pixel area of a CCD sensor to acquire the wavelength spectra, that the pixel area and/or the dispersing device are arranged relative to the first matrix of holes with such an inclination that the wavelength spectra of the foci imaged in the first holes impact the pixel surface without any overlap.

32. The method of claim 29, wherein the pixel surface and/or the dispersing device are arranged at an inclination relative to the first matrix of holes in such a manner that the wavelength spectra of the foci imaged in the first holes contact each other without any free pixels.

33. The method of claim 29, wherein a first spectrum of a focus is determined, that an optical element that changes the path length of the beam path is arranged in the optical path of the focus, that a second spectrum is determined from the focus with changed beam path, that the spectra are subtracted from each other, and that from the resulting equal peaks with opposite sign, the wavelength of the light of the focus is determined.

34. The method of claim 29, wherein the spectral curve of the background of the spectrum of the focus is determined by determining spectra of light reaching second holes associated with the first holes, whereby the arrangement of the second holes deviates from the arrangement of the multi-focal illumination pattern.

35. The method of claim 29, wherein spectra of light of several second holes associated with one first hole are averaged for the purpose of determining the background.

36. The method of claim 29, wherein the object is measured intraorally.

37. The method of claim 29, wherein for measuring the object, sections of the object are measured one after the other, whereby subsequent sections possess a common subsection that constitutes between 50% and 95% of the size of the section.

38. The method of claim 29, wherein for determining the shape of the at least one section of the object, the subsections are recorded subsequently with a frame rate of between 25 and 50 images per second.

39. The method of claim 29, wherein for the purpose of imaging the sections, a deflecting device that is arranged between the object and the objective lens is moved.

40. The method of claim 29, wherein for the purpose of imaging the sections, the deflecting device and the object are moved as a unit.

41. The method of claim 29, wherein for measuring the sections, the multi-focal illumination pattern is moved, and the first matrix of holes is moved synchronously.

42. The method of claim 29, wherein the object is imaged onto an image-acquisition device, whereby for the imaging a spectral region is selected, in which the illumination pattern imaged on the object is imaged out of focus.

* * * * *